United States Patent [19]

Ohshima et al.

[11] Patent Number: 5,359,123
[45] Date of Patent: Oct. 25, 1994

[54] POLYOXYALKYLENE POLYAMINES HAVING SECONDARY AMINO GROUPS

[75] Inventors: Toshiyuki Ohshima, Ibaraki; Hideo Ishibashi, Neyagawa; Rie Tamura, Toyonaka; Satoshi Yamamoto, Hirakata; Takaharu Izumo, Shimamoto, all of Japan

[73] Assignee: Nippon Paint Co., Ltd., Osaka, Japan

[21] Appl. No.: 37,823

[22] Filed: Mar. 29, 1993

Related U.S. Application Data

[63] Continuation-in-part of Ser. No. 834,100, Feb. 12, 1992, abandoned.

[51] Int. Cl.$^5$ .................. C07C 69/66; C07C 229/08; C08G 18/32; C09K 3/00
[52] U.S. Cl. ...................... 560/39; 560/169; 252/182.27; 528/73; 528/75; 528/77
[58] Field of Search ............... 558/452, 467; 560/169, 560/39; 562/564; 564/305, 434, 505; 252/182.27; 528/73, 75, 77

[56] References Cited

U.S. PATENT DOCUMENTS

| | | | |
|---|---|---|---|
| 2,787,633 | 4/1957 | Harrison et al. | 558/452 |
| 2,982,782 | 5/1961 | Selcer | 558/452 |
| 3,247,163 | 4/1966 | Reinking | 560/169 X |
| 3,496,138 | 2/1970 | Sellers et al. | 564/505 X |
| 3,666,788 | 5/1972 | Rowton | 564/505 X |
| 3,770,798 | 11/1973 | Norton | 558/452 X |
| 4,240,804 | 12/1980 | Shield | 560/169 X |
| 4,711,737 | 12/1987 | Burgoyne et al. | 564/305 X |

OTHER PUBLICATIONS

Grigsby et al, J. Elastomers and Plastics, vol. 23, pp. 54 to 65 (1991).
Bruson, "Adams Organic Reactions", vol. V, pp. 79 to 87, 108 to 110, 114, and 115 (1949).
Grigsby et al, "Journal of Elastomers and Plastics," vol. 23, pp. 54–65 (1991).

*Primary Examiner*—Floyd D. Higel
*Attorney, Agent, or Firm*—Millen, White, Zelano & Branigan

[57] ABSTRACT

Trifunctional polyoxyalkylene polyamines having a plurality of 2-alkoxycarbonylethylamino groups at terminals are produced by reacting the corresponding primary amines with an alkyl acrylate. The trifunction secondary polyamines thus produced have a moderate reaction rate with a polyisocyanate component in polyurea RIM.

6 Claims, No Drawings

POLYOXYALKYLENE POLYAMINES HAVING SECONDARY AMINO GROUPS

This application is a continuation-in-part of application Ser. No. 07/834,100 filed Feb. 12, 1992, now abandoned.

BACKGROUND OF THE INVENTION

This invention relates to polyoxyalkylene polyamines having secondary amino groups at their terminals.

Polyoxyalkylene polyamines find use as a polyamine component of polyurea elastomers, polyurea reaction injection molding (RIM) and other polyurea products. One of disadvantages of polyoxyalkylene polyamines is the increased reaction rate with polyisocyanates. Thus, they tend to cause premature curing when used in polyurea RIM. This is particularly true when the polyoxyalkylene polyamine is trifunctional because the resulting polyurea polymer assumes a three dimentional network structure.

It has been known that the reaction rate of a primary polyoxyalkylen polyamine with a polyisocyanate may be decreased by modifying the primary amine to the corresponding secondary amine. See, R. A. Grigsby, Jr. and D. M. Rice, "Modified Polyetheramines in RIM", J. Elastomers and Plastics, 23, 54–65 (1991). One of such modification methods comprises the cyanoethylation of primary amino groups with acrylonitrile which is known to be highly toxic, explosive and flammable.

U.S. Pat. No. 4,431,790 corresponding to EP-A-0046088 discloses a secondary polyoxyalkylene polyamine produced by reacting the corresponding primary amine with a hydroxyalkyl acrylate or methacrylate.

This patent also discloses that the reaction product has a significantly decreased reactivity with a polyisocyanate compared to the starting primary amine and thus is useful as a curing agent in the manufacture of polyurethane polymers from polyols and polyisocyanates. It has been discovered, however, that polyoxyalkylene polyamines modified with a hydroxyalkyl acrylate or methacrylate still tend to cause premature curing in the absence of a polyol.

U.S. Pat. No. 5,075,503 issued Dec. 24, 1991 disclosese hydrazine terminated polyoxyalkylene polyamines useful as latent epoxy curing agents or chain extenders for polyurea polymers. The hydrazine terminated polyetherpolyamines are synthesized by the two step reaction of reacting a polyoxyalkylene diamine with an alkyl acrylate followed by the aminolysis of the resulting adduct with hydrazine. This patent, however, does not address to the secondarization of trifunctional polyoxyalkylene polyamines which are more acute than the secondarization of the corresponding diamines in the polyurea RIM.

Accordingly, a need exists for a trifunctional secondary polyoxyalkylene polyamines having a moderate reactivity in the polyurea RIM.

SUMMARY OF THE INVENTION

The above need may be met, according to the present invention, by providing a trifunctional polyoxyalkylene polyamine having a plurality of 2-alkoxyethylamino groups of the formula:

—NH—CH$_2$CH$_2$COOR wherein R is an alkyl. The alkoxyethylamino-terminated polyoxyalkylene triamine of the present invention may be produced by a Michael type-addition reaction of an alkyl acrylate with the corresponding primary polyoxyalkylene triamine.

In a preferred embodiment, the acrylate is of a C$_{4\text{-}10}$ alkyl such as n-butyl or 2-ethylhexyl acrylate and the starting polyoxyalkylene triamine is a polyoxypropylene triamine having an amino equivalent greater than 1,000.

DESCRIPTION OF THE PREFERRED EMBODIMENT

The production of the secondary polyoxyalkylene triamine of the present invention involves the following Michael type-addition reaction.

—NH$_2$+CH$_2$=CH$_2$—COOR→—NHCH$_2$CH$_2$COOR

Starting primary polyamines used in the present invention include trifunctional polyoxyalkylene polyamines which are conventionally used in the polyurea RIM.

Polyoxyalkylene polyamines having a plurality of primary amino groups at the terminals of the molecule may be produced as disclosed, for example, in Belgian Patent No. 677124 by the hydrogenolytic ammonolysis of the corresponding polyoxyalkylene polyols.

A variety of polyoxyalkylene polyamines are commercially available including polyoxypropylene triamines sold under the name of Texrim TR-5050 (Texaco Chemical, amine equivalent about 1930) and Jeffamine T-403 (Texaco Chemical, amine equivalent about 160). Texrim TR series having an amine equivalent greater than 1,000 may advantageously be used in the present invention.

Examples of alkyl acrylates include methyl acrylate, ethyl acrylate, propyl acrylate, n-butyl acrylate, isobutyl acrylate, t-butyl acrylate, 2-ethylhexyl acrylate, lauryl acrylate and sstearyl acrylate. Acrylates of C$_{4\text{-}10}$ alkyls are preferable.

We have discovered that the Michael reaction of the primary polyamine and the alkyl acrylate may unexpectedly promoted by the presence of an acidic or neutral esterification catalyst. Particularly, the presence of such a catalyst is practically imperative when a high percent conversion is desired with a polyoxyalkylen polyamine having a high molecular weight.

Examples of usable catalysts include inorganic or organic acid such as hydrochloric, sufuric, nitric, phosphoric, propionic, formic, acetic, dischloroacetic, trichloroacetic, trifluoroacetic, benzoic or p-toluenesulfonic acid; unitary metal oxides such as aluminum oxide, silicon oxide and niobium oxide; complexed metal oxides such as SiO$_2$/Al$_2$O$_3$, TiO$_2$/SiO$_2$, SiO$_2$/La$_2$O$_3$ and TiO$_2$/Al$_2$O$_3$; sulfides such as zinc sulfide; sulfate such as nickel sulfate and copper sulfate; phosphates such as aluminum phosphate and titanium phosphate; chloride such as aluminum chloride and copper chloride; clays such as acid clay, montmorillonite and kaolin; solidified acids such as solidifed phosphoric acid, solidified sulfuric acid and solidified boric acid; and acidic ion exchange resins. Also included are organotin compounds such as dibutyltin oxide and dibutyltin dilaurate; organoaluminum compounds such as aluminum isopropylate, mono-sec.-butoxyaluminum diisopropylate, aluminum ethylate, aluminum ethylacetoacetate diisopropylate, aluminum tris-ethylacetoacetate and aluminum bis-ethylacetoacetate monoacetylacetonate; organotitanium compounds such as tetraisopropoxytitanium, tetra-n-butoxytitanium, tetrakis-2-ethylhexoxytitanium, tetrakis-stearyloxytitanium, diisopropoxybis(acetylacetonato)titanium, di-n-butoxy-bis(triethanollammine)titanium and hydroxy-bis(lactato)titanium.

We have also discovered that the Michael reaction of the primary polyoxyalkylene polyamine and the alkyl acrylate may be promoted by the presence of a benzenoid compound having at least one electron-donating or electron-withdrawing substituent on the benzene ring in place of or in addition to the esterification catalyst. Quinones are also useful for promoting the Michael reaction. Examples of useful benzenoid compounds and quinones include alkyl or aralkyl-substituted benzenoids such as toluene, xylene, ethylbenzene, t-butylbenzene and diphenylmethane; aromatic amines such as aniline, N,N-dimethylaniline, diaminotoluene, xylidine, diaminodiphenylmethane, bis-(N-ethylamino)toluene and aminonaphthalene; hydroxyl compounds such as phenol, cresol and naphthol; halo compounds such as fluorobenzene, chlorobenzene, bromobenzene, iodobenzene, chloronaphthalene and iodonaphthalene; nitro compounds such as nitrobenzene, dinitrotoluene and dinitronaphthalene; cyano compounds such as benzonitrile and naphthonitrile; ketones such as acetophenone and propiophenone; benzenoid compounds having a combination of mentioned substituents; and quinones such as benzoquinone and naphthoquinone.

The ratio of the alkyl acrylate relative to the starting polyamine may vary within a wide range as desired. This ratio in terms of equivalent of ethylenic function relative to the primary amine function may range from 0.01 to 100, preferable from 1 to 10. This means that the presence of a minor amount of unreacted primary amine functions or ethylenic functions may be tolerated in the reaction mixture.

The amount of the esterification catalyst may vary, when used, but should be no more than the catalytically effective amount.

The amount of aromatic compounds having an electron-donating or withdrawing group should be no more than the tolerable limit in the modified polyoxyalkylene polyamine composition. This amount is generally no more than one equivalent relative to the primary amine function of the starting polyoxyalkylene polyamine.

The Michael reaction may be performed at a temperature from room temperature to about 150° C. After the reaction, the reaction mixture may be used as such as a raw material in the polyurea RIM and the like. If the reaction mixture includes an amount of unreacted alkyl acrylate and/or catalyst, these impurities may be removed by polymerizing, neutralizing or other suitable means.

The following examples are intended to further illustrate the present invention without limiting thereto. All parts and percents therein are by weight unless otherwise indicated.

EXAMPLE 1

A 500 ml flask equipped with a stirrer, reflux condenser, drip funnel, thermometer and nitrogen gas tube was charged with 386g of Texrim TR-5050(trifunctional polyoxypropylene polyamine, amine equivalent 1930, average MW 5000) and heated to 120° C. To this was added 73.6 g of 2-ethylhexyl acrylate dropwise over 4 hours and allowed to react for additional 24 hours. The percent conversion of the reaction mixture into secondary amine was measured by the salicylaldehyde method according to the modified Wagner method (C. D. Wagner et al., J.Am Chem. Soc., 69, 2609–2611 (1947). The result is shown in Table 1. The percent conversion represents the per cent of secondary amine number relative to the total amine number.

EXAMPLE 2

To the same reactor as used in Example 1 were placed 386 g of Texrim TR-5050 and 19.8 g of diaminodiphenylmethane. Then 73.6 g of 2-ethylhexy acrylate was added dropwise over 4 hours and allowed to react for additional 36 hours. The per cent conversion is shown in Table 1.

EXAMPLE 3

Example 2 was repeated except that 17.8 g of diethyltolylenediamine was replaced for diamino-diphenylmethane. The per cent conversion is shown in Table 1.

EXAMPLE 4

Example 2 was repeated except that 18.6 g of aniline replaced for diaminodiphenylmethane. The per cent conversion is shown in Table 1.

EXAMPLE 5

Example 2 was repeated except that 21.2 g of ethylbenzene was replaced for diaminodiphenylmethane. The per cent conversion is shown in Table 1.

EXAMPLE 6

Example 2 was repeated except that 51.2 g of n-butyl acrylate was replaced for 2-ethylhexyl acrylate and the reaction was continued for 20 hours. The per cent conversion is shown in Table 1.

EXAMPLE 7

To the same reactor as used in Example 1 was placed 200 g of Jeffamine T-403 (trifunctional polyoxyalkylene polyamine, amine equivalent 160, average MW 400). To this was added 230 g of 2-ethylhexyl acrylate dropwise over 2 hours and allowed to react for additional 3 hours. The per cent conversion is shown in Table 1.

EXAMPLE 8

The same reactor as used in Example 1 was charged with 360 g of Texrim TR-5050 and 0.6 g of acetic acid, and heated to 120° C. To this was added 73.6 g 2-ethylhexyl acrylate dropwise over 4 hours and allowed to react for additional 4 hours. The per cent conversion is shown in Table 2.

EXAMPLE 9

Example 8 was repeated except that 1.9 g of p-toluenesulfonic acid was replaced for acetic acid. The per cent conversion is shown in Table 2.

EXAMPLE 10

Example 9 was repeated except that 36.8 g of 2-ethylhexyl acrylate was added dropwise over 2 hours and allowed to react for additional 6 hours. The per cent conversion is shown in Table 2.

EXAMPLE 11

Example 9 was repeated except that 51.2 g of n-butyl acrylate was replaced for 2-ethylhexyl acrylate. The per cent conversion is shown in Table 2.

EXAMPLE 12

Example 8 was repeated except that 20 g of solidified phosphoric acid E48A1 ($P_2O_5/SiO_2/TiO_2$ type sold by JGC Corporation) was replaced for acetic acid. The per cent conversion is shown in Table 2.

EXAMPLE 13

Example 8 was repeated except that 20 g of silicaalumina catalyst N631HN (JGC Corporation) was replaced for acetic acid. The per cent conversion is shown in Table 2.

EXAMPLE 14

Example 8 was repeated except that 3.4 g of tetrabutoxytitanium was replaced for acetic acid. The per cent conversion is shown in Table 2.

EXAMPLE 15

Example 8 was repeated except that 6.3 g of dibutyltin dilaurate was replaced for acetic acid. The per cent conversion is shown in Table 2.

EXAMPLE 16

The same reactor used in Example 1 was charged with 200 g of Jeffamine T-403 and 11.9 g of p-toluene sulfonic acid, and heated to 80° C. To this was added 230 g of 2-ethylhexyl acrylate dropwise over 2 hours and allowed to react for additional 3 hours. The per cent conversion is shown in Table 2.

TABLE 1

| Example No. | Polyoxyalkylene Polyamine(a) | Monomeric Compound(b) | Aromatic Compd.(c) | Equivatent ratio a:b:c | Reaction temp., °C. | Reaction time, hr. | % Conversion |
|---|---|---|---|---|---|---|---|
| 1 | TR-5050 | 2-EHA[1] | — | 1:2:0 | 120 | 28 | 38 |
| 2 | TR-5050 | 2-EHA | DDM[3] | 1:2:1 | 120 | 40 | 86 |
| 3 | TR-5050 | 2-EHA | DETDA[4] | 1:2:1 | 120 | 40 | 87 |
| 4 | TR-5050 | 2-EHA | Aniline | 1:2:1 | 120 | 40 | 85 |
| 5 | TR-5050 | 2-EHA | Ethylbenzene | 1:2:1 | 120 | 40 | 85 |
| 6 | TR-5050 | nBA[2] | DDM | 1:2:1 | 120 | 20 | 79 |
| 7 | T-403 | 2-EHA | — | 1:1:0 | 80 | 5 | 80 |

Footnote of Table 1
[1] 2-Ethylhexyl acrylate
[2] n-Butyl acrylate
[3] Diaminodiphenylmethane
[4] Diethyltolylenediamine

TABLE 2

| Example No. | Polyoxyalkylene Polyamine(a) | Monomeric Compound(b) | Aromatic Compd.(c) | Equivatent ratio a:b:c | Reaction temp., °C. | Reaction time, hr. | % Conversion |
|---|---|---|---|---|---|---|---|
| 8 | TR-5050 | 2-EHA | ACOH | 1:2:0.05 | 120 | 8 | 96 |
| 9 | TR-5050 | 2-EHA | PTS[1] | 1:2:0.05 | 120 | 8 | 97 |
| 10 | TR-5050 | 2-EHA | PTS | 1:1:0.05 | 120 | 8 | 80 |
| 11 | TR-5050 | nBA | PTS | 1:2:0.05 | 120 | 8 | 95 |
| 12 | TR-5050 | 2-EHA | E48A1 | 1:2:x[3] | 120 | 8 | 90 |
| 13 | TR-5050 | 2-EHA | N631HN | 1:2:x | 120 | 16 | 57 |
| 14 | TR-5050 | 2-EHA | Ti(OBu)$_4$ | 1:2:0.05 | 120 | 16 | 60 |
| 15 | TR-5050 | 2-EHA | DBTDL[2] | 1:2:0.05 | 120 | 12 | 97 |
| 16 | T-403 | 2-EHA | PTS | 1:2:0.05 | 80 | 3 | 98 |

Footnote of Table 2
[1] p-Toluenesulfonic acid
[2] Dibutyltin dilaurate
[3] Not applicable

We claim:

1. A composition consisting essentially of a trifunctional secondary polyoxyalkylene polyamine having a plurality of terminal secondary amino groups of the formula:

$$-NH-CH_2CH_2COOR$$

wherein R is an alkyl of from 4–10 carbon atoms.

2. The composition of claim 1 further containing a minor proportion of a trifunction primary amine corresponding to said trifunctional secondary amine.

3. The composition of claim 1, wherein said polyoxyalkylene polyamine is a polyoxypropylene triamine.

4. The composition of claim 3, wherein said polyoxypropylene triamine has an amine equivalent greater than 1,000.

5. The composition of claim 1, wherein said alkyl is n-butyl.

6. The composition of claim 1, wherein said alkyl is 2-ethylhexyl.

* * * * *